United States Patent [19]

Alig et al.

[11] Patent Number: 5,057,527
[45] Date of Patent: Oct. 15, 1991

[54] METHOD OF PREVENTING INFESTATION OF FLEAS

[75] Inventors: Bernd Alig, Koenigswinter; Wilhelm Stendel, Wuppertal; Michael Londershausen, Erkrath, all of Fed. Rep. of Germany

[73] Assignee: Bayer Aktiengesellschaft, Leverkusen, Fed. Rep. of Germany

[21] Appl. No.: 376,340

[22] Filed: Jul. 6, 1989

[30] Foreign Application Priority Data

Jul. 23, 1988 [DE] Fed. Rep. of Germany ....... 3825172

[51] Int. Cl.$^5$ ..................... A61K 31/44; C07D 237/02
[52] U.S. Cl. .................................. 514/345; 514/247; 514/255; 514/269; 544/239; 544/298; 544/408; 546/296; 546/297; 546/301; 546/302
[58] Field of Search ................ 514/345; 546/301, 302, 546/296, 297

[56] References Cited

U.S. PATENT DOCUMENTS 4,751,225 6/1988 Nishida et al. ...................... 514/345

FOREIGN PATENT DOCUMENTS 60-215671 10/1985 Japan .

Primary Examiner—Nicholas S. Rizzo
Assistant Examiner—Jyothsna Venkai
Attorney, Agent, or Firm—Sprung Horn Kramer & Woods

[57] ABSTRACT

The present invention relates to the use of substituted alkoxydiphenyl ethers or alkoxydiphenylmethanes of the general formula I

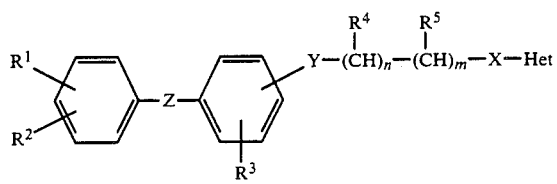

in which
 $R^1$ represents hydrogen, halogen, alkyl, alkoxy, alkylthio, halogenoalkyl, halogenoalkoxy, halogenoalkylthio, dioxalkylene, dioxyhalogenoalkylene, CN, $NO_2$, alkenyl, alkinyl, alkoxyalkyl, alkoxyalkoxy or hydroxyalkoxy,
 $R^2$ represents the radicals indicated for $R^1$,
 $R^3$ represents the radicals indicated for $R^1$,
 $R^4$ represents hydrogen, alkyl, halogenoalkyl or halogen,
 $R^5$ represents the radicals indicated for $R^4$,
 Het represents optionally substituted heteroaryl which is not linked to the remaining radical via the hetero atom,
 X, Y independently of one another represent —O— or —S—
 Z represents —O—, —S—, —$CH_2$—, —$CHCH_3$— or —$C(CH_3)_2$—,
 m and n independently of one another represent 0, 1, 2 or 3 but their total is equal to, or more than, 2 are exceedingly suitable for controlling fleas.

1 Claim, No Drawings

METHOD OF PREVENTING INFESTATION OF FLEAS

The present invention relates to the use of substituted alkoxydiphenyl ethers and alkoxydiphenylmethanes for controlling fleas on pets.

Alkoxydiphenyl ethers and alkoxy diphenylmethanes and their insecticidal action have already been disclosed (EP-OS (European Published Specification) 128,648). However, nothing has been disclosed about their action against fleas.

Adult fleas usually live in the coat of the host animals. They feed on their blood and lay their eggs in the coat of the host animal.

Since the eggs laid do not adhere to the coat of hair, they fall off rapidly and can be found everywhere in the surroundings of the host animals, for example beds and beddings. This means that the complete habitat of the host animals is infected with flea eggs from which flea larvae hatch within a few days. Three developmental stages can be distinguished in the larvae, each of which lasts approx. three days. The 3rd larval stage spins a cocoon and pupates. Under favorable conditions (20°–30° C., 60–70% relative atmospheric humidity), the development from the egg to the pupa lasts approx. 10 days. After about 8 more days, development of the fleas is complete, and fleas which are ready to hatch can be found in the cocoons lying on the floor, carpets, sleeping places, etc. The young flea can remain in its cocoon for months. Under unfavorable conditions, however, the development from the egg to the young adult flea can last as long as 4 to 5 months. In order to reach sexual maturity, that is to say for laying complete eggs, fleas require blood as food. Ideally, this blood is from the particular specific host. However, particularly after a relatively long fasting period, fleas can also accept the blood of other hosts.

Infestation with fleas of pets such as dogs and cats is not only a nuisance for the infested animal but also causes considerable pain to the infested animals. Moreover, fleas can spread various species of tapeworm. Thus, they also represent a medical problem to the infested animals and to the animal keepers. It is also possible that the animal keeper is bitten by fleas. In some humans, this causes allergy to flea bites. For this reason, effective control of fleas in dogs and cats has always been desirable and necessary since these pets live in increasingly close contact with man.

Fleas on pets which live together with man, such as, for example, dogs and cats, are controlled
1. by treating the host animal,
2. by treating the beds of the host animal,
3. by treating the complete surrounding of the host animal, that is to say the dwelling and the areas outside the dwelling of the human.

Treatment of the beds and the surrounding of the host animal is particularly important for thorough flea control. Treatment of the host animal alone is of little promise since for weeks and even months there is danger of re-infestation by freshly hatched young fleas from the surroundings. The treatment of beds and surroundings is particularly promising when not only the adult fleas but also the developmental stages which occur separately from the host animal can be influenced.

It is known that the treatment can be carried out with insecticides, such as, for example, phosphoric acid esters, carbamates, or natural and synthetic pyrethroids.

The active compounds which are employed here must not only have low toxicity to warm-blooded animals but also a long-term action in order to avoid too frequent treatments. Moreover, the active compounds must be active against both adult and larval stages of the flea. Some of the above-mentioned active compounds are only specifically active and hence too short a duration of action, and some of them are toxic and can only be applied when particular precaution measures are observed.

It is also known that insect growth regulators such as methoprene can be employed for controlling fleas. However, methoprene can is unstable and must thus be employed in relatively high concentrations in order to be active over a relatively long period of time. On the other hand, methoprene is not active against adult fleas. Re-infestation with fleas is thus easily possible, moreover, direct pestering of humans and animals by the adult fleas is not remedied.

Due to these shortcomings of the known insecticides and growth regulators, there was a demand for active compounds against fleas or individual developmental stages of the fleas, which are highly-active and stable and have a low toxicity to warm-blooded animals.

It has now been found that substituted alkoxy-diphenyl ethers or alkoxydiphenylmethanes of the general formula I

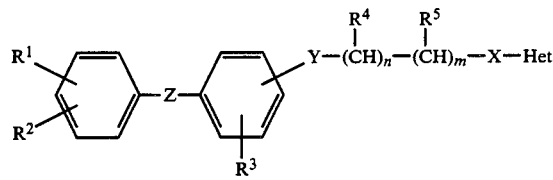

in which $R^1$ represents hydrogen, halogen, alkyl, alkoxy, alkylthio, halogenoalkyl, halogenoalkoxy, halogenoalkylthio, dioxalkylene, dioxyhalogenoalkylene, CN, NO$_2$, alkenyl, alkinyl, alkoxyalkyl, alkoxyalkoxy or hydroxyalkoxy, $R^2$ represents the radicals indicated for $R^1$, $R^3$ represents the radicals indicated for $R^1$, $R^4$ represents hydrogen, alkyl, halogenalkyl, or halogen, $R^5$ represents the radicals indicated for $R^4$, Het represents optionally substituted heteroaryl which is not linked to the remaining radical via the hetero atom, X, Y independently of one another represent —O— or —S—

Z represents —O—, —S—, —CH$_2$—, —CHCH$_3$— or —C(CH$_3$)$_2$—, m and n independently of one another represent 0, 1, 2 or 3 but their total is equal to, or more than, 2 are exceedingly suitable for controlling fleas.

As already mentioned, it was disclosed in EP-OS (European Published Specification) 128,648 that compounds of the formula I are insecticidally active as insect growth regulators. This is also known with reference to various noxious insects, such as, for example, *Galleria mellonella, Culex pipiens pallens, Musca domestica* and spider mites, for exmaple *Tetranychus cinnabarinus.*

However, nothing is evident from this reference about the excellent suitability of these compounds for controlling fleas. The type of action of the compounds is similar to juvenile hormones. It is extremely difficult especially for compounds having such actions just to clearly predict if they are active against an order of insects which differs clearly from the insects described as far as their lifestyle and their developmental cycle are concerned.

It is possible, for example, to clearly predict the insecticidal activity over all orders and developmental stages of insects even when this activity has been proved on only few species when the activity is based on a mechanism which is common to all orders and developmental stages. This includes, for example, inhibition of acetylcholine esterase by phosphoric acid esters, carbamates and pyrethroids. These compounds act, for example, neurotoxically.

On examination of the maximum differences in activity which are characteristic within one substance class for individual orders and species of insects, only a slight variation is found in insecticides which are classified as neurotoxic compared with the insecticides coming under the growth regulators. That is to say, the differences between the concentrations of individual active compounds which are active for individual orders of insects are relatively small.

This is different in the case of active compounds which influence insect development, such as, for example, in the case of juvenile hormone analogous compounds. In these compounds, there are large differences between the concentrations of individual active compounds which are active against various insect orders.

In order to compare such differences from the literature data, variation factors were calculated from the amounts of substance applied per $\mu g$ of animal fresh weight or per $\mu g$ of animal by dividing, for each active compound, the maximum application rate required by the minimum application rate required. This factor is a measure of the varying application rates which are necessary for an active compound for different insect orders.

A comparison of neurotoxic active compounds (212 substances) and compounds which are juvenoidally active or act as a development inhibitor (330 substances) against various insect orders showed mean variation factors of approx. 51 for the neurotoxic insecticides and 2187 for the development inhibitors which also include the juvenile hormone analogues.

The data on which the calculation of these variation factors was based were taken from the following references:

1) C. A. Hendrick, 1982
*JUVENILE HORMONE ANALOGS: STRUCTURE-ACTIVITY RELATIONSHIPS* In: Insecticide Mode of Action, 11 (314-402), Ed: J. R. Coats, Academic Press 2) G. S. F. Ruigt, 1985
*PYRETHROIDS*
In: Comprehensive Insect Physiology Biochemistry and Pharmacology, 12 (184-262), Eds: G. A. Kerkut and G. I. Gilbert, Pergamon Press 3) C. O. Knowles, 1982
*STRUCTURE-ACTIVITY RELATIONSHIPS AMONG AMIDINE ACARICIDES AND INSECTICIDES*
In: Insecticides Mode of Action, 9 (243-277), Ed: J. R. Coats, Academic Press 4) T. A. Magee, 1982
*OXIME CARBAMATE INSECTICIDES*
In: Insecticide Mode of Action 4 (71-100), Ed: J. R. Coats, Academic Press 5) H. Ohkawa, 1982
*STEREOSELECTIVITY OF ORGANOPHOSPHORUS INSECTICIDES*
In: Insecticide Mode of Action, 6 (163-185), Ed: J. R. Coats, Academic Press 6) A. Retnakaran and J. E. Wright, 1987
*CONTROL OF INSECT PESTS WITH BENZOYL-PHENYL-UREAS*
In: Chitin and Benzoylphenyl-Ureas, Eds: J. D. Wright and A. Retnakran, Dr. J. Junk Publishers In the various references, and due to the test set-ups, the $LC_{50}$ or $LC_{95}$ values are based on ppm values (in the nutrient medium), or the amounts of substance applied per animal or animal fresh weight are indicated which is then evaluated in the activity determination as $\mu g$/animal or $\mu g$/animal fresh weight.

Inconsistent dimensions of this type can be found when juvenile hormone mimics are compared (*Aedes aegypti* and *Heliothis virescens* values are indicated in ppm, but values for Galleria, Tenebrio and Musca in $\mu g$ per animal: Ref. 1). Since the variation factors of both determination types cannot be compared, the ppm values were evaluated separately from the $\mu g$/animal value, and the $\mu g$/animal values were continued on a $\mu g$/animal fresh weight basis so that the entirely different animal sizes/weights have a common basis. This resulted in the following factors with which the data are multiplied in order to have a basis:

TABLE

| Species | g fresh weight mean | n | Factor |
|---|---|---|---|
| 1 *Galleria mellonella* | 0.400 g/pupa | 5 | 2.50 |
| 2 *Tenebrio molitor* | 0.61 g/pupa | 12 | 6.25 |
| 3 *Musca domestica* | 0.034 g/pre-pupa | 100 | 29.41 |

Values in which all the $\mu g$/animal values were >100 factor for all three species (approx. 11% of all JH mimics tested) and generally the determinations without individual values were not included in the evaluation.

The following individual values were obtained:

| Substance classes | Variation factor (x) | Standard deviation/ mean $S_{n-1}/x$ | Number of active compounds n |
|---|---|---|---|
| Neurotoxic insecticides: | | | |
| Organophosphates | 125 | 1.43 | 12 |
| Carbamates | 45 | 1.82 | 130 |
| Pyrethroids | 4.4 | 2.47 | 51 |
| Amidines | 29 | 0.80 | 19 |
| Growth regulators: | | | |
| Benzoylphenyl-ureas | 2970 | 1.99 | 6 |
| Juvenile hormone mimics (ug/g fresh weight values) | 2727 | 3.11 | 177 |
| Juvenile hormone mimics (ppm values) | 865 | 1.80 | 147 |

It can be seen from the values that the variation between effective and ineffective concentrations are considerably larger in the case of juvenile hormone-active compounds than in the case of neurotoxically active compounds.

This finding means that on average the action on an insect species which had not been tested can be predicted better in the area of the neurotoxic insecticides, even where the dose/sensitivity relations of various insect order and species are different, than is possible in the case of growth regulators.

The comparison between the means variation factors of neurotoxic insecticides (x=50.85) and growth regulators (x=2187) shows that the action of neurotoxic insecticides can be predicted more accurately by a factor of 43 (2187:50.85) than is the case in the case of the growth regulators.

This can also be illustrated with reference to the following example.

The different action of very similar juvenile hormone mimics within one species, and the partly completely reversed activity of the comparison compounds in the case of a different insect species are more pronounced in the case of the growth regulators than in the case of neurotoxic substances. The activities of the two active compounds indicated below were calculated per unit weight from reference 1 (above) and from G. B. Staal, 1982, *INSECT CONTROL WITH GROWTH REGULATORS INTERFERING WITH THE ENDOCRINE SYSTEM*, Ent. Exp. & appl. 31, 15-23.

| Substance | Acyrthosiphon pisum | Aedes aegypti | Heliothis viresc. | Galleria mellon | Tenebrio molit. | Musca dom. |
|---|---|---|---|---|---|---|
| 1 | 100 | 1 | 3 | 33 | 1 | 1 |
| 2 | 1 | 12 | 1 | 1 | 2255 | 1429 |

Here it can be seen that 1 has a good action on *Acyrthosiphon pisum* and *Galleria mellonella*, where 2 shows only little action. On the other hand, 2 has a good action on *Tenebrio molitor* and *Musca domestica* where 1 shows only little action.

This example shows how difficult it is to reliably predict the action, especially in the case of growth-regulating compounds.

However, this means that even if EP-OS (European Published Specification) 128,648 disclosed that the compounds of the formula I have insecticidal activity, it cannot be concluded from this that they are highly active especially against fleas (Siphonaptera).

The fleas include: *Pulex irritans, xenopsylla cheopis, ctenocephalides canis, Ctenocephalides felis, ceratophyllus gallinae, Echidnophaga gallinacea* and *Tunga penetrans*.

Preferred compounds of the formula I are those in which $R^1$ represents hydrogen, fluorine, chlorine, bromine, $C_{1-4}$-alkyl, $C_{1-4}$-alkoxy, $C_{1-4}$-alkylthio, $C_{1-4}$-halogenoalkyl having up to 5 halogen atoms, in particular trichloromethyl, trifluoromethyl, $C_{1-4}$-halogenoalkoxy having up to 5 halogen atoms in particular trichlormethoxy, trifluoromethoxy, $C_{1-4}$-halogenoalkylthio having up to 4 halogen atoms in particular trifluoroemethylthio, CN, $NO_2$, $C_{2-3}$-alkenyl, $C_{1-4}$-alkoxy-$C_{1-2}$-alkyl, in particular ethoxymethyl, methoxyethyl, $C_{1-2}$-alkoxy-$C_{1-4}$-alkoxy in particular methoxyethoxy, $C_{1-4}$-hydroxyalkoxy in particular hydroxyethoxy, dioxyethylene, dioxymethylene, difluorodioxymethylene, trifluorodioxymethylene or dichlorooxymethylene, $R^2$ represents the radicals incidated for $R^1$,
$R^3$ represents the radicals indicated for $R^1$,
$R^4$ represents hydrogen, $C_{1-4}$-alkyl, $C_{1-4}$-halogenoalkyl having approx. 5 halogen atoms, chlorine, fluorine or bromine,
$R^5$ represents the radicals indicated for $R^4$,
Het represents pyridyl, pyridazinyl, pyrimidinyl or pyrazinyl which is substituted optionally by one or more identical or different radicals from the series comprising $C_{1-4}$-alkyl, such as methyl, ethyl, t-butyl, halogen such as fluorine, chlorine or bromine, $NO_2$, $C_{1-4}$-alkoxy, $C_{1-4}$-alkylthio, $C_{1-4}$-halogenoalkyl having up to 5 halogen atoms, $C_{1-4}$-halogenoalkoxy having up to 5 halogen atoms or $C_{1-4}$-halogenoalkylthio having up to 5 halogen atoms,
X, Y independently of one another represent —O— or —S—,
Z represents —O—, —S—, —CH$_2$—, —CHCH$_3$— or —C(CH$_3$)$_2$—,
m represents 1 or 2,
n represents 1 or 2.

Particularly preferred compounds of the formula I are those in which
$R^1$ represents hydrogen, methyl, trifluoromethyl, methoxy, trifluormethoxy, chlorine or fluorine
$R^2$ represents hydrogen,
$R^3$ represents hydrogen, fluorine, chlorine or methyl,
$R^4$ represents hydrogen or methyl,
$R^5$ represents methyl, ethyl, trifluoromethyl or hydrogen,
Het represents pyridyl or pyridazinyl which are optionally substituted by fluorine, chlorine, methyl, $NO_2$, methoxy or methylmercapto,
X represents 0,
Y represents 0,
Z represents 0, $CH_2$ or —C(CH$_3$)$_2$—,
m represents 1,
n represents 1.

The following compounds may be mentioned individually:

| $R^1$ | $R^3$ | $R^5$ | $R^6$ | Z |
|---|---|---|---|---|

-continued

| | | | | |
|---|---|---|---|---|
| H | H | CH₃ | H | O |
| H | H | CH₃ | 2-Cl | O |
| 5-F | H | CH₃ | H | O |
| H | H | CF₃ | H | O |
| H | H | C₂H₅ | H | O |
| H | H | H | H | O |
| H | H | CH₃ | H | CH₂ |
| H | H | CH₃ | H | C(CH₃)₂ |

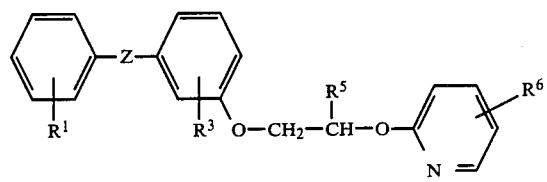

| $R^1$ | $R^3$ | $R^5$ | $R^6$ | Z |
|---|---|---|---|---|
| H | H | CH₃ | H | O |

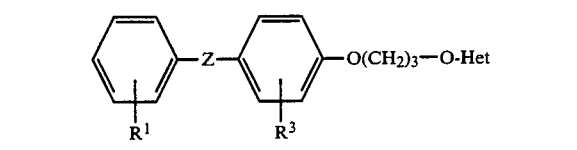

| $R^1$ | $R^3$ | Z | Het |
|---|---|---|---|
| H | H | O | |
| H | H | O | |
| H | H | O | |

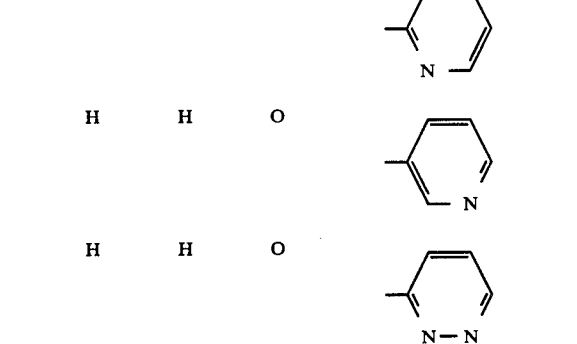

The active compounds are applied directly or in the form of suitable preparations, dermally, enterally or parenterally, or by treating the surroundings, or with the aid of active compound-containing shaped articles, such as, for example, bands, neckbands, limb bands or marking devices.

Dermal application is carried out, for example, in the form of dipping, spraying, pouring-on and spotting-on, and powdering.

Preparations for dermal application are, for example, solutions, suspension concentrates, emulsion concentrates and microemulsions which are diluted with water prior to application, formulations for pouring-on, powders and dusts, aerosols and active compound-containing shaped articles.

Solutions, suspension concentrates, emulsion concentrates and microemulsions which are diluted with water prior to application, powders, dusts and aerosol formulations are employed for the treatment of the surroundings of the pets.

These formulations are prepared in a known manner, for example by mixing the active compound with extenders, that is to say, for example liquid solvents, optionally with the use of surface-active agents, that is to say emulsifying agents and/or dispersing agents. In the event that water is used as an extender, organic solvents can, for example, also be used as auxiliary solvents.

Besides water, liquid diluents include alcohols, such as methanol, ethanol, isopropanol, n-butanol, amyl alcohol or octanol; glycols, such as propylene glycol, 1,3-butylene glycol, ethyl glycol or dipropylene glycol monomethyl ether; glycerol; aromatic alcohols, such as benzyl alcohol; carboxylic acid ethers, such as, for example, ethyl acetate, benzyl benzoate, butyl acetate, propylene carbonate or ethyl lactate; aliphatic hydrocarbons, such as paraffins, cyclohexane, methylene chloride or ethylene chloride; aromatic hydrocarbons, such as xylene, toluene, alkylnaphthalenes or chlorobenzenes; ketones, such as, for example, acetone and methyl ethyl ketone, methyl isobutyl ketone or cyclohexanone; natural and synthetic mono- and tri-glycerides with natural fatty acids, such as cottonseed oil, groundnut oil, maize germ oil, olive oil, castor oil or sesame oil; furthermore dimethyl sulphoxide, dimethylacetamide, dimethylformamide, N-methylpyrrolidone, dioxane or 2,2-dimethyl-4-oxymethyl-1,3-dioxolane.

The surface-active substances include: emulsifiers and wetting agents, such as anion-active surfactants, for example alkylsulphonates, alkyl sulphates, arylsulphonates, sodium lauryl sulphates, fatty alcohol ether sulphates, the monoethanolamine salt of mono/dialkyl polyglycol ether orthophosphoric ester or calcium alkylarylsulphonate; cation-active surfactants, for example cetyltrimethylammonium chloride; ampholytic surfactants, for example disodium N-lauryl beta-iminodipropionate or lecithin; non-ionogenic surfactants, for example polyoxyethylated castor oil, polyoxyethylated sorbitan monooleate, polyoxyethylated sorbitan monostearate, glycerol monostearate, polyoxyethylene stearate, alkylphenol polyglycol ethers, polyoxyethylated sorbitan monopalmitate, polyoxyethylene lauryl ether, polyoxyethylene oleyl ether, polyoxyethylene mannitan monolaurate, alkyl polyglycol ethers, oleyl polyglycol ethers, dodecyl polyglycol ethers, ethoxylated nonylphenol or isooctylphenolpolyethoxyethanol.

Moreover, the preparations can contain: adhesives, for example carboxymethylcellulose, methylcellulose and other cellulose and starch derivatives, polyacrylates, alginates, gelatin, gum arabic, polyvinylpyrrolidone, polyvinyl alcohol, methyl vinyl ether/maleic anhydride copolymers, polyethylene glycols, paraffins, oils, waxes, hydrogenated castor oil, lecithins and synthetic phospholipids.

The preparations can contain colorants, such as inorganic pigments, for example iron oxide, titanium oxide, Prussian Blue, and organic pigments, such as alizarin, azo and metal phthalocyanine dyes.

The preparations can contain spreading agents, for example silicone oils of various viscosities, fatty acid esters, such as ethyl stearate, di-n-butyl adipate, hexyl laurate, dipropylene glycol pelargonate, esters of a branched fatty acid of medium chain length with saturated fatty alcohols C₁₆-C₁₈, isopropyl myristate, isopropyl palmitate, caprylic/capric acid esters of saturated fatty alcohols of chain length C₁₂-C₁₈, isopropyl stearate, oleyl oleate, decyl oleate, ethyl oleate, ethyl lactate, waxy fatty acid esters, dibutyl phthalate, diisopropyl adipate, ester mixtures related to the latter and the like; triglycerides such as carylic/capric acid triglyceride, triglyceride mixtures with vegetable fatty acids of chain length C₈-C₁₂ or other specially selected natural fatty acids, mixtures of partial glycerides of saturated or unsaturated fatty acids which may contain hydroxyl groups, monodiglycerides of $C_8/C_{10}$-fatty acids and others; fatty alcohols such as isotridecyl alcohol, 2-octyldodecanol, cetylstearyl alcohol or oleyl alcohol.

To prepare powders and dusts, the active compound is mixed with suitable carriers, if necessary using additives, and shaped as desired.

Carriers which may be mentioned are all physiologically acceptable solid inert substances. Inorganic and organic substances are used. Inorganic substances are optionally crushed and fractioned, for example synthetic and natural, ground minerals such as kaolins, talc, chalk, diatomaceous earth, common salt, aluminas, silicas, clays, preciptitated or colloidal silicon dixoide. Organic substances are lactose, starch and cellulose or cellulose derivatives.

Auxiliaries are preservatives, antioxidants or colorants which have already been mentioned further above.

Other suitable auxiliaries are lubricating and slipping agents, such as, for example, magnesium stearate, stearic acid, talc or bentonites.

The active compounds can also be used in form of an aerosol. For this purpose, the active compound is finely distributed under pressure in a suitable formulation.

It can also be advantageous to apply the active compounds in formulations which release the active compound slowly. As such formulations, active compound-containing shaped articles, such as, for example, plates, ribbons, strips, neckbands, limb bands or marking devices may be mentioned.

The active compounds can be present in the formulations on their own or in a mixture with other active compounds or synergists.

Formulations which are applied directly contain between $10^{-7}$ and 5 percent by weight, preferably between $10^{-4}$ and 1 percent by weight, of active compound.

Formulations which are only used after further dilution contain 1–95 percent by weight, preferably 5–90 percent by weight, of active compound.

Formulation Examples

1. Preparation of an emulsion concentrate

| (a) Active compound of Example 1 (100%) | 25.00 g |
|---|---|
| Non-ionic emulsifier (Emulgator 368 ® = alkylaryl polyglycol ether MW approx. 1165) | 25.00 g |
| Dipropylene glycol monomethyl ether to | 100.00 ml |

Preparation

The substances are weighed together and stirred until a clear solution has formed. The solution is diluted to its application concentration prior to use.

| (b) Active compound of Example 2 (100%) | 1.00 g |
|---|---|
| Polyoxyethylene stearate | 0.50 g |
| Sorbitan sesquioleate | 0.40 g |
| Water | 4.00 g |
| Polyethylene glycol 200 to | 100 ml |

Preparation and use as in 1a

2. Preparation of a pour-on formulation

| (a) Composition | |
|---|---|
| Active compound of Example 1 (100%) | 5.00 g |
| Isopropyl myristate | 30.00 g |
| 2-Octyldodecanol | 20.00 g |
| Isopropanol to | 100 ml |

Preparation

The substances are weighed together and stirred until a clear solution has formed.

| (b) Composition | |
|---|---|
| Active compound of Example 1 (100%) | 0.50 g |
| Silicone oil 100 | 30.00 g |
| Butyl acetate to | 100 ml |

Preparation as in Example a)

3. Preparation of a microemulsion

| Active compound of Example 1 (100%) | 13.00 g |
|---|---|
| Eumulgin B3 ® (alkylaryl polyglycol ether) | 30.00 g |
| Cetiol HE ® (polyol fatty acid ester) | 30.00 g |
| Isopropyl myristate | 5.00 g |
| Benzyl alcohol | 3.00 g |
| Water to | 100 ml |

Preparation

The active compound is dispersed in the lipophilic components (Eumulgin, Cetiol, benzyl alcohol and isopropyl myristate).

The mixture is warmed to 60° C., water of the same temperature is admixed, and the mixture is cooled. The microemulsion formed superficially resembles a clear solution.

4. Preparation of a spray formulation

| Composition | |
|---|---|
| Active compound of Example 1 (100%) | 20 g |
| Emulgator Toximul ® (mixture of calcium alkylbenzene-sulphonate and non-ionogenic emulsifiers and methanol) | 7 g |
| Emulgator Toximul S ® (mixture of calcium alkylbenzene-sulphonate and non-ionogenic emulsifier and methanol) | 5 g |
| Sovesso 200 ® to (alkylnaphthalene mixture of high-boiling mineral oil fractions) | 100 ml |

Preparation

The active compound is weighed together with the remaining components, and the mixture is stirred and diluted with water to the application concentration prior to use.

Preparation of active compounds

EXAMPLE 1

12.6 g of 1-methyl-2-(4-phenoxyphenoxy)-ethanol and 13 g of 2-chloropyridine are refluxed for 24 hours in 200 ml of toluene together with 12 g of NaOH powder, 8 g of $K_2CO_3$ powder and 0.8 g of the phase transfer catalyst tris-(3,6-dioxaheptyl)amine. After the mixture has cooled down, the tolene phase is washed with water, dried over $Na_2SO_4$ and concentrated in vacuo. The residue is subsequently distilled. Yield: 9.5 g, boiling point 250° C./0.4 mm.

The following compounds were prepared analogously:

EXAMPLE 2

$^1$H-NMR, $CDCl_3$: 7.5–6.62 ppm (m, 12H, 9-aromat. H+H-3'+H-4'+H-5'); 5.55 ppm (m, $CH_B$, 1H); 4.18–4.05 ppm (m, 2H, $CH_{2A}$); 1.48 ppm (d,3H, J=7.5 Hz, $CH_{3C}$).

Boiling point: 250° C./0.2 mm
Yield: 33% of theory

EXAMPLE 3

$^1$H-NMR, $CDCl_3$: 8.1 ppm (m, H-6'); 7.5 ppm (m, H-4'); 7.35 ppm–6.55 ppm (m, 11 H, 9-aromat. H+H-3'+H-5'); 5.55 ppm (m, 1H, $CH_B$); 4.15 ppm–4.02 ppm (m, 2H, $CH_{2A}$); 1.45 ppm (d, J=6, 6 Hz, 3H, $CH_{3C}$).

Boiling point: 230° C.–250° C./0.2 mm
Yield: 25% of theory

EXAMPLE 4

Boiling point: 250° C./0.2 mm
Yield: 16% of theory

EXAMPLE 5

$^1$H-NMR, $CDCl_3$: 8.12 ppm (m, 1H, H-6'); 7.55 ppm (m, 1H, H-4'); 7.29–6.73 ppm (m, 11H, 9-aromat. H+H-3'+H-5'); 5.46 ppm (m, 1H, —CH—O—); 4.16 ppm (m, 2H, $CH_{2A}$); 1.93 ppm (m, 2H, $CH_{2B}$); 1.04 ppm (t, J=6,5 Hz, 3H, $CH_3$).

Yield: 40% of theory

EXAMPLE 6

$^1$H-NMR, $CDCl_3$: 8.15 ppm (m, H-6'); 7.58 ppm (m, H-4'); 7.32–6.90 ppm (m, 9H, aromate.); 6.88 ppm (m, H-5'); 6.81 ppm (m, H-3'); 4.68 ppm (t, J=4.9 Hz, $CH_{2B}$); 4.31 ppm (t, $CH_{2A}$).

Boiling point: 250° C./0.3 mm
Yield: 66% of theory

EXAMPLE 7

$^H$-NMR, $CDCl_3$: 8.16'8.14 ppm (m, H-6'); 7.59–7.53 ppm (m, H-4'); 7.31–6.83 ppm (m, 10 H, 9-aromat. H+H-5'); 6.73 ppm (m, H-3'); 4.49 ppm (t, J=6.2 Hz; $CH_{2C}$); 4.13 ppm (t, $CH_{2A}$); 2.26 ppm (quint., $CH_{2B}$).

Yield: 56% of theory

EXAMPLE 8

$^1$NRM, $CDCl_3$: 8.1 ppm (m, H-6'); 7.55 ppm (m, H-4'); 7.32–6.70 ppm (m, 11 H, 9-aromat. H+h-3'+H-5'); 5.55 ppm (m, 1H, CH); 4.15–4.02 ppm (m, 2H, $CH_{2B}$); 3.88 ppm (s, $CH_{2A}$); 1.45 ppm (d, J=7Hz, $CH_3$).

Yield: 40% of theory

EXAMPLE 9

$^1$H-NMR, DMSO: 8.16 (m, H-6'); 7.69 ppm (m, H-4'); 7.28–6.77 ppm (m, 11H, 9-aromat. H+H-3'+H-5'); 5.50 ppm (m, CH); 4.17–4.05 ppm (m, 2H, $CH_2$); 1.60 ppm (s, 6H, $$-C\begin{array}{c}CH_3\\ \\ CH_3\end{array});$$

1.34 ppm (d, J=6.4 Hz, $CH_3$).
Yield: 45% of theory

USE EXAMPLES

A. In-vitro test on fleas (all developmental stages)
Test object: All stages (eggs, larvae, pupae, adults) of *Ctenocephalides felis*

Testing procedure

The substance to be tested is distributed homogeneously in blood meal in the concentration desired. Flea eggs which had been collected from flea-injested cats were transferred into this mixture of blood meal and test substance, and everything was incubated at 80% relative atomospheric humidity at 25° C.

After the development time of 3-4 weeks has elapsed, it is determined if adult fleas have developed. 100% action signifies that no adult fleas have been determined.

At a concentration of 5 ppm, the compound of Example 2 has an action of 100%.

B. In-vivo test on fleas (all developmental stages)
Test object: Eggs, larvae, pupae of *Ctenocephalides felis* in the environment of dogs/cats, adult fleas on dogs/cats.

Testing procedure

Beds, in boxes, of dogs/cats which are free of fleas are sprayed with the substance to be tested in the desired application concentration. At certain points in time after application, eggs of *Ctenocephalides felis* which had been collected from treated cats are transferred to the beds of the dogs/cats. It is determined if and at which point in time the dogs/cats in the boxes were infested by adult fleas.

Here, a 100% action signifies that dogs/cats show no infestation with fleas and 0% action that dogs/cats are infested with fleas.

The compound of Example 2 has an action of 100%.

What is claimed is:

1. A method of preventing infestation of fleas of the genera Ctenocephalides comprising applying to said fleas, their hosts or their habitat $10^{-4}$–5% by weight of an alkoxydiphenyl ether of the formula

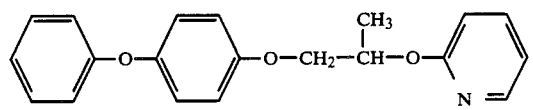

* * * * *